(12) United States Patent
Simonson

(10) Patent No.: US 7,708,764 B2
(45) Date of Patent: *May 4, 2010

(54) METHOD FOR CREATING AN ARTIFICIAL FACET

(76) Inventor: Peter M. Simonson, 85 Palm Ave., Miami Beach, FL (US) 33139

( * ) Notice: Subject to any disclaimer, the term of this patent is extended or adjusted under 35 U.S.C. 154(b) by 0 days.

This patent is subject to a terminal disclaimer.

(21) Appl. No.: 10/720,659

(22) Filed: Nov. 24, 2003

(65) Prior Publication Data

US 2005/0101954 A1   May 12, 2005

Related U.S. Application Data

(63) Continuation-in-part of application No. 10/704,868, filed on Nov. 10, 2003, now abandoned.

(51) Int. Cl.
*A61B 17/88* (2006.01)
(52) U.S. Cl. .................................. 606/279; 606/247
(58) Field of Classification Search ................ 606/61, 606/246–279; 623/17.11–17.16
See application file for complete search history.

(56) References Cited

U.S. PATENT DOCUMENTS

| 3,219,575 A | 11/1965 | Chapman et al. |
| 3,242,922 A | 3/1966 | Thomas |
| 3,565,066 A | 2/1971 | Roaf |
| 4,269,178 A | 5/1981 | Keene |
| 4,272,401 A | 6/1981 | Mohan et al. |
| 4,361,141 A | 11/1982 | Tanner |
| 4,369,769 A | 1/1983 | Edwards |
| 4,369,770 A | 1/1983 | Bacal et al. |
| 4,382,438 A | 5/1983 | Jacobs |
| 4,386,603 A | 6/1983 | Mayfield |
| 4,404,967 A | 9/1983 | Bacal et al. |
| 4,409,968 A | 10/1983 | Drummond |
| 4,411,259 A | 10/1983 | Drummond |
| 4,419,026 A | 12/1983 | Leto |
| 4,422,451 A | 12/1983 | Kalamchi |
| 4,448,191 A | 5/1984 | Rodnyansky et al. |
| 4,567,884 A | 2/1986 | Edwards |
| 4,611,582 A | 9/1986 | Duff |
| 4,662,365 A | 5/1987 | Gotzen et al. |
| 4,743,260 A | 5/1988 | Burton |
| 4,773,402 A | 9/1988 | Asher et al. |
| 4,815,453 A | 3/1989 | Cotrel |

(Continued)

FOREIGN PATENT DOCUMENTS

EP    0516567    5/1992

OTHER PUBLICATIONS

Spine-Health.Com, "Facet Technologies," http://www.spine-health.com/research/discupdate/artificial/artificia106.html.

(Continued)

*Primary Examiner*—Thomas C Barrett
*Assistant Examiner*—James L. Swiger
(74) *Attorney, Agent, or Firm*—Novak Druce + Quigg; Gregory A. Nelson

(57) ABSTRACT

An artificial facet joint includes a spinal implant rod and a connector. The connector includes a screw and a rod connecting member having structure for engagement of the rod. The rod connecting member is pivotally engaged to the screw.

13 Claims, 8 Drawing Sheets

U.S. PATENT DOCUMENTS

| | | | |
|---|---|---|---|
| 4,836,196 A | 6/1989 | Park et al. | |
| 4,854,304 A | 8/1989 | Zielke | |
| 4,887,595 A | 12/1989 | Heinig et al. | |
| 4,887,596 A | 12/1989 | Sherman | |
| 4,946,458 A | 8/1990 | Harms et al. | |
| 4,950,269 A | 8/1990 | Gaines, Jr. | |
| 4,987,892 A | 1/1991 | Krag et al. | |
| 5,002,542 A | 3/1991 | Frigg | |
| 5,005,562 A | 4/1991 | Cotrel | |
| 5,024,213 A | 6/1991 | Asher et al. | |
| 5,102,412 A | 4/1992 | Rogozinski | |
| 5,127,912 A | 7/1992 | Ray et al. | |
| 5,129,900 A | 7/1992 | Asher et al. | |
| 5,133,717 A | 7/1992 | Chopin | |
| 5,147,360 A | 9/1992 | Dubousset | |
| 5,181,917 A | 1/1993 | Rogozinski | |
| 5,209,752 A | 5/1993 | Ashman et al. | |
| 5,246,442 A | 9/1993 | Ashman et al. | |
| 5,257,993 A | 11/1993 | Asher et al. | |
| 5,261,909 A | 11/1993 | Sutterlin et al. | |
| 5,282,801 A | 2/1994 | Sherman | |
| 5,282,901 A | 2/1994 | Reinhard | |
| 5,312,404 A | 5/1994 | Asher et al. | |
| 5,409,488 A * | 4/1995 | Ulrich | 606/61 |
| 5,415,661 A | 5/1995 | Holmes | |
| 5,437,669 A | 8/1995 | Yuan et al. | |
| 5,437,670 A | 8/1995 | Sherman et al. | |
| 5,437,671 A * | 8/1995 | Lozier et al. | 606/61 |
| 5,474,551 A * | 12/1995 | Finn et al. | 606/61 |
| 5,486,174 A * | 1/1996 | Fournet-Fayard et al. | 606/61 |
| 5,498,262 A | 3/1996 | Bryan | |
| 5,549,608 A | 8/1996 | Errico et al. | |
| 5,554,157 A * | 9/1996 | Errico et al. | 606/61 |
| 5,562,662 A | 10/1996 | Brumfield et al. | |
| 5,569,247 A | 10/1996 | Morrison | |
| 5,571,191 A | 11/1996 | Fitz | |
| 5,575,791 A * | 11/1996 | Lin | 606/61 |
| 5,591,166 A | 1/1997 | Bernhardt et al. | |
| 5,609,592 A * | 3/1997 | Brumfield et al. | 606/250 |
| 5,611,800 A | 3/1997 | Davis et al. | |
| 5,634,925 A * | 6/1997 | Urbanski | 606/61 |
| 5,643,259 A * | 7/1997 | Sasso et al. | 606/61 |
| 5,672,175 A | 9/1997 | Martin | |
| 5,693,053 A | 12/1997 | Estes | |
| 5,716,357 A | 2/1998 | Rogozinski | |
| 5,800,435 A | 9/1998 | Errico et al. | |
| 5,876,459 A | 3/1999 | Powell | |
| 5,879,351 A * | 3/1999 | Viart | 606/61 |
| 5,891,145 A | 4/1999 | Morrison et al. | |
| 5,938,663 A * | 8/1999 | Petreto | 606/61 |
| RE36,758 E | 6/2000 | Fitz | |
| 6,183,473 B1 | 2/2001 | Ashman | |
| 6,210,413 B1 | 4/2001 | Justis et al. | |
| 6,241,730 B1 | 6/2001 | Alby | |
| 6,248,105 B1 | 6/2001 | Schlapfer et al. | |
| 6,328,739 B1 | 12/2001 | Liu et al. | |
| 6,413,257 B1 | 7/2002 | Lin et al. | |
| 6,443,956 B1 | 9/2002 | Ray | |
| 6,554,831 B1 | 4/2003 | Rivard et al. | |
| 6,562,038 B1 * | 5/2003 | Morrison | 606/278 |
| 6,565,565 B1 | 5/2003 | Yuan et al. | |
| 6,579,319 B2 | 6/2003 | Goble et al. | |
| 6,623,485 B2 | 9/2003 | Doubler et al. | |
| 6,648,887 B2 | 11/2003 | Ashman | |
| 6,676,661 B1 * | 1/2004 | Martin Benlloch et al. | 606/61 |
| 6,685,705 B1 * | 2/2004 | Taylor | 606/61 |
| 6,966,930 B2 | 11/2005 | Arnin et al. | |
| 7,083,622 B2 * | 8/2006 | Simonson | 606/61 |
| 2003/0004572 A1 | 1/2003 | Goble et al. | |
| 2003/0028250 A1 | 2/2003 | Reiley et al. | |
| 2003/0045874 A1 | 3/2003 | Thomas, Jr. | |
| 2003/0083657 A1 * | 5/2003 | Drewry et al. | 606/61 |
| 2003/0083659 A1 | 5/2003 | Lin et al. | |
| 2003/0139745 A1 * | 7/2003 | Ashman | 606/61 |
| 2004/0092934 A1 * | 5/2004 | Howland | 606/61 |
| 2005/0261682 A1 | 11/2005 | Ferree | |

OTHER PUBLICATIONS

Zimmer Spine, "DYNESYS, The Dynamic Stabilization System (U.S. only)," http://www.zimmerspine.com/spine/products/lumbar/dynesys/index.

* cited by examiner

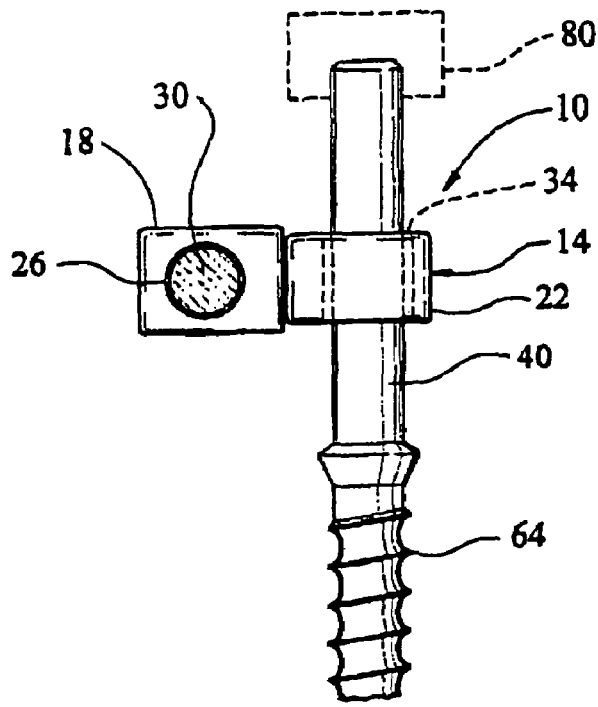
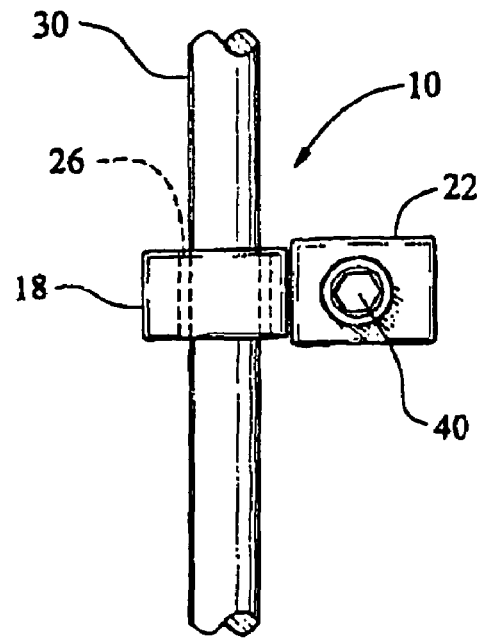
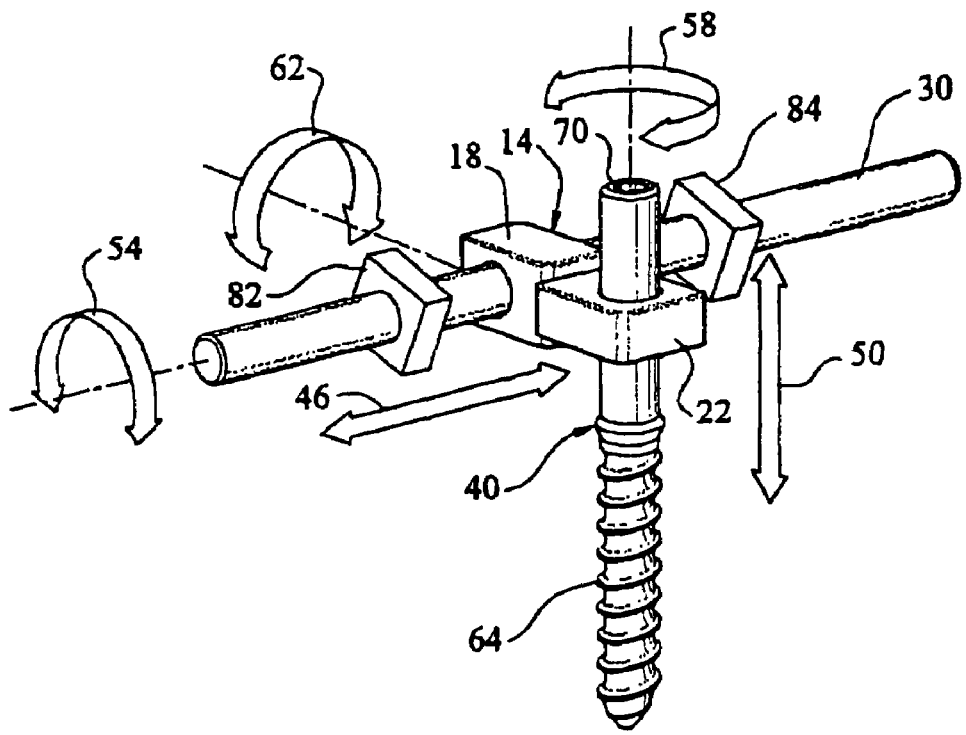
FIG. 1
FIG. 2
FIG. 3

METHOD FOR CREATING AN ARTIFICIAL FACET

CROSS-REFERENCE TO RELATED APPLICATIONS,

This application is a continuation-in-part application of Applicant's application Ser. No. 10/704,868, filed Nov. 10, 2003 now abandoned.

STATEMENT REGARDING FEDERALLY SPONSORED RESEARCH OR DEVELOPMENT

Not applicable.

FIELD OF THE INVENTION

This invention relates generally to the field of artificial joints and more particularly to artificial joints and ligaments.

BACKGROUND OF THE INVENTION

Each vertebra in the human spine has two sets of joints which interact with adjacent upper and lower joints. These joints are known as the facet joints, and are otherwise known as the zygapophyseal or apophyseal joints. Two joints are formed on each lateral side of the vertebra. The superior articular facet faces upward and the inferior articular facet faces downward, such that the superior articular facet of a lower vertebrae abuts the inferior articular facet of an adjacent upper vertebrae. The facet joints are located on the posterior of the spine adjacent the pedicle, lamina, and transverse process. The facet joints generally are hinge-like and allow limited flexion, extension, and twisting motion, while preventing excessive motion which could damage the spinal chord.

Various spinal reconstructive or treatment procedures require the removal of the facet joint and ligament structures. The joint and ligament must then be reconstructed artificially. Known artificial facet joints fail to provide the rigidity that is necessary to support the spine while permitting the flexibility to reassemble the facet joint.

SUMMARY OF THE INVENTION

An artificial facet joint includes a pair of connectors. Each connector comprises a first device connecting member having structure for sliding engagement of a rod and a second device connecting member having structure for sliding engagement of a screw. The first device connecting member and second device connecting member are rotatably engaged to one another. A spinal implant rod and a pair of spinal implant screws are provided. The first device connecting member of each of the connectors is slidably engaged to the rod. The second device connecting member of each of the connectors is slidably engaged to a respective one of the pair of spinal implant screws. The screws can be engaged to the pedicles on one lateral side of adjacent vertebra and the rods and connectors will limit movement of the joint. Structure for securing the spinal implant rod against axial movement relative to the spine can be provided. The structure for sliding engagement of the rod can be an aperture and the structure for sliding engagement of a screw can be an aperture. The apertures of the first device connecting member and the second device connecting member can comprise a reduced friction coating.

The artificial facet joint can further comprise a second pair of connectors, a second spinal implant rod and a second pair of second implant screws. The second pair of screws can be engaged to the pedicles of the other lateral side of the adjacent vertebra and the second rod and second pair of connectors will limit movement of the joint on the other lateral side of the adjacent vertebra. A transverse member can be connected between the first and second rod. The transverse member can be slidably engaged to the first and second rods. The transverse member can alternatively be connected between screws.

The artificial facet joint can further comprise structure for securing the rod to a portion of the spine. This structure can comprise a clamp for the rod and structure for securing the clamp to a screw. Alternatively, the structure can comprise blocking members on the rod.

The spinal implant rod can include structure for engaging the first device connecting member so as to limit the sliding movement of the rod relative to the first device connecting member. The spinal implant screw can comprise structure for engaging the second device connecting member so as to limit the sliding movement of the rod relative to the second device connecting member.

A connector for an artificial facet joint includes a first device connecting member having structure for sliding engagement of a spinal implant rod and a second device connecting member having structure for sliding engagement of a spinal implant screw. The first device connecting member and second device connecting member are rotatably engaged to one another. The structure for engaging the first device connecting member can be an aperture and the structure for engaging the second device connecting member can be an aperture. The apertures of the first device connecting member and the second device connecting member can comprise a reduced friction coating.

A connector assembly for an artificial joint can include a connection device having a first connecting portion with structure for sliding engagement of a rod and a second connecting portion with sliding engagement of a screw. A spinal implant rod is slidably engaged to the first connecting portion and the spinal implant screw is slidably engaged to the second connecting portion. The structure for engaging the rod can be an aperture and the structure for engaging the screw can be an aperture. The spinal implant rod can comprise structure for engaging the first connecting portion so as to limit the sliding movement of the rod relative to the first connecting portion. The spinal implant screw can comprise structure for engaging the second connecting portion so as to limit the sliding movement of the rod relative to the second connecting portion.

An artificial facet joint includes a spinal implant rod and connector. The connector comprises a first device connecting member having structure for sliding engagement of said rod and a second device connecting member having structure for sliding engagement of a screw. The first device connecting member and second device connecting member are rotatably engaged to one another. Structure is provided for securing the spinal implant rod against axial movement relative to the spine.

A method for creating an artificial facet joint includes the step of providing a first pair of connectors. Each connector comprises a rod connecting member having an aperture for engaging a rod, screw connecting member having an aperture for engaging a screw, the rod connecting member and the screw connecting member being rotatably engaged to one another. A first screw is secured to a pedicle of a first vertebra. A second screw is secured to a pedicle of a second vertebra. The screws can be positioned in the plane of the facet. The screw connecting member of the first connector is slidably engaged to the first screw, and the screw connecting member of the second connector is slidably engaged to the second screw. A spinal implant rod is slidably engaged to the rod connecting member of the first connector and to the rod connecting member of the second connector. The rod is then secured.

A second pair of connectors can be provided. Each connector comprises a rod connecting member having an aperture for engaging a rod and a screw connecting member having an aperture for engaging a screw. The rod connecting member and the screw connecting member are rotatably engaged to one another. A first screw is secured to a pedicle on an opposite lateral side of a first vertebra. A second screw is secured to a pedicle on an opposite side of a second vertebra. The screw connecting member of the first connector is slidably engaged to the first screw and the screw connecting member of the second connector is slidably engaged to the second screw. A spinal implant rod is slidably engaged to the rod connecting member of the first connector of the second pair of connectors and to the rod connecting member of the second connector on the opposite lateral side of the vertebra. The second rod is secured between the second pair of connectors. A transverse member can be attached between the spinal implant rods.

A spinal joint assembly includes a spinal joint device joined to a spinal implant rod which is capable of post-operative sliding movement relative to the rod. Structure can be provided for limiting the length of sliding movement between the spinal implant rod and the spinal joint device. A method of connecting a spinal joint assembly to a spine includes the steps of connecting a spinal implant rod to a spine and attaching a spinal implant device to the rod. The device is capable of post-operative sliding movement relative to the rod.

A spinal joint assembly comprises a spinal joint device joined to a spinal implant screw. The spinal joint device is capable of post-operative sliding movement relative to the screw. Structure can be provided for limiting the length of sliding movement between the spinal implant screw and the spinal joint device. A method of connecting a spinal joint assembly to a spine includes the steps of connecting a spinal implant screw having a long axis to the spine. A spinal implant device is connected to the screw and is capable of post-operative sliding movement along the long axis of the screw.

A bone implant screw is provided for securing connected implants to a spine. The bone implant screw upon installation in the spine permits dorsal movement relative to itself and the connected implants. The screw can comprise a post. The movement permitted by the screw can further comprise rotation of the connected implants about an axis of the screw. The screw can comprise structure for limiting dorsal movement of the connected implants beyond a range of movement.

An artificial facet joint comprises a spinal implant rod and a connector. The connector comprises a screw and a rod connecting member having structure for engagement of the rod. The rod connecting member is pivotally engaged to the screw. The rod connecting member can be detachable from the screw. The pivoting can be about a pivot point substantially in the long axis of the screw. The connector can be polyaxially pivotable relative to the rod.

The connector can engage the rod to prevent sliding movement of the rod relative to the connector. The connector can alternatively permit sliding movement of the rod relative to the connector. The connector can comprise a saddle portion and a detachable cap for enclosing the rod within the saddle portion.

Structure can be provided for limiting the angulation of the rod connector relative to the screw. This structure can provide increasing resistance as the degree of angulation increases. The structure can comprise a stop on at least one of the connector and the screw. The stop can comprise an elastic material.

The artificial facet joint can further comprise a second spinal implant rod and a second connector. The second connector can comprise a screw and a rod connecting member having structure for engagement of the rod. The rod connecting member is pivotally engaged to the screw. A transverse crosslinking member engages and connects the spinal rods. The crosslinking member can engage the rods and contact the connectors to limit movement of the spinal rods relative to the connectors.

An artificial facet joint can comprise a spinal implant rod and a connector with a rod connecting portion and a screw portion. The connector permits sliding movement of the rod relative to the rod connecting portion and pivoting of the rod relative to the screw portion. The pivot can be about a pivot point substantially in the long axis of the screw.

An artificial facet joint can comprise a spinal implant rod and a connector with a rod connecting portion and a screw portion. The connector engages the rod to prevent sliding movement of the rod relative to the rod connecting portion and permits pivoting of the rod relative to the screw portion. The pivot can be about a pivot point substantially in the long axis of the screw.

An artificial facet joint can comprise a spinal implant rod and a fixation connector with a rod engaging portion and a screw portion. The fixation connector engages the rod to prevent sliding movement of the rod relative to the rod engaging portion and permits pivoting of the rod relative to the screw portion. A sliding connector has a rod connecting portion and a screw portion. The sliding connector permits sliding movement of the rod relative to the rod connecting portion and pivoting of the rod relative to the screw portion.

An artificial facet joint comprises a spinal rod that is substantially parallel to the spinal column and can span at least three vertebrae.

An artificial facet joint comprises a spinal rod that articulates in the sagittal plane.

An artificial facet joint can connect vertebral bodies of adjacent vertebrae on the same lateral side of the spine with a single rod.

The artificial facet joints can be implanted by suitable methods. In one method, only percutaneous incisions are needed to install the artificial facet joint.

An artificial facet joint can comprise a spinal implant rod and at least one connector for sliding engagement of the rod. The connector can further have structure for engaging the spine. The rod has a shape defining a desired bending of the spine, such that bending of the spine will cause sliding movement of the connector relative to the rod. The rod will guide the connector according to a path defined by the rod.

An artificial facet joint can comprise a spinal implant rod and at least one connector for engaging the rod to a screw. The connector is movable over the screw. The screw is shaped to provide a path for guiding the motion of the spine during bending of the spine.

BRIEF DESCRIPTION OF THE DRAWINGS

There are shown in the drawings embodiments which are presently preferred, it being understood, however, that the invention is not limited to the precise arrangements and instrumentalities shown, wherein:

FIG. 1 is a side elevation of a connector.

FIG. 2 is a plan view.

FIG. 3 is a perspective view of a connection assembly with a connector, spinal implant rod, and a spinal implant screw, illustrating by arrows the motion that is possible.

DETAILED DESCRIPTION OF THE INVENTION

Figure 4:
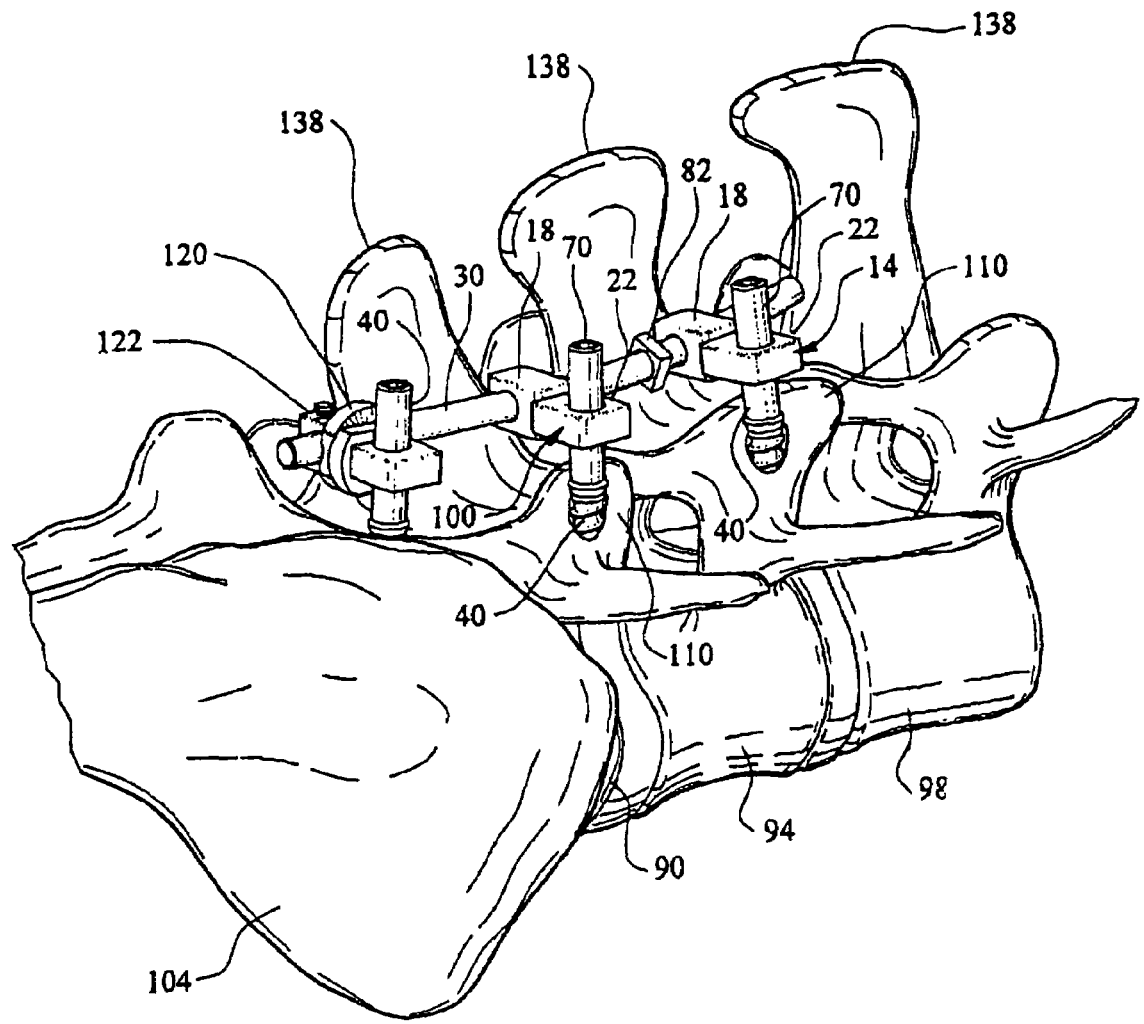
FIG. 4 is a perspective view of an artificial facet joint according to the invention as implanted in a spine.

There is shown in FIGS. 1-3 a connector assembly for an artificial facet joint according to the invention. The connector assembly 10 includes a connector 14 having a first device connecting member 18 and a second device connecting member 22. The first device connecting member 18 has structure for sliding engagement of a spinal implant rod 30. The second device connecting member 22 has structure for sliding engagement of a spinal implant screw 40. The structure for slidably engaging the spinal implant rod 30 can be an aperture 26 for receiving the rod 30. The structure for slidably engaging the spinal implant screw 40 can be an aperture 34 for receiving the screw 40. Other structure is possible. The apertures 26 and 34 can be larger in diameter than the cross-sectional diameter of the rod 38 and screw 40, if desired, to permit movement of the first device connecting member 18 relative to the rod 30 as shown by arrow 46 in FIG. 3, as well as transverse movement to the extent of the size of the aperture 26. Similarly, the size of the aperture 34 can permit movement of the second device connecting member 22 relative to the screw 40, as shown by arrow 50 in FIG. 3, as well as transverse movement to the extent of the size of the aperture 34. Also, the first device connecting member 18 can rotate about the rod 30, as shown by arrow 54, and second device connecting member can rotate about the screw 40, as shown by arrow 58.

The first device connecting member 18 and second device connecting member 22 are rotationally engaged to one another such that the first device connecting member 18 can rotate relative to the second device connecting member 22 as indicated by arrow 62 in FIG. 3. Any suitable connecting structure which will secure the first connecting member 18 to the second connecting member 22 and permit this rotation can be used.

The screw 40 can be any suitable spinal implant or pedicle screw or bolt. Threads 64 are provided for engaging the bone, however, other constructions for securing the device to bone are possible. The elongated shaft 70 can be of sufficient length that the second device connecting member 22 does not become disengaged. The shape of the screw head shaft may be varied to produce a desired motion path similar to a particular facet joint. For example, the screw shaft may have a curved shape. Alternatively, it is possible to place a head or cap unit on the screw 40. The head unit 80 (phantom lines in FIG. 1) would be an enlarged portion which could either be detachable from the screw 40 or form a permanent part thereof. The head 80 has a diameter larger than that of the aperture 34 such that the second device connecting member 22 cannot be removed from the screw 40. Other structure is possible.

The screw can also have an irregular cross section, such as an elipse, so that a connecting device can be attached which makes for the irregular shape and prevents rotation of the connecting device relative to the screw. The screw can alternatively have a protrusion or other engagement structure which engages a corresponding recession or cooperating engagement structure in the connecting device to prevent rotation.

It is also possible to limit the range of movement of the rod 30 within the first device connecting member 18. This can be accomplished by a blocking portion 82 that is provided on the rod 30 and is large enough so as not to permit passage through the aperture 26 of the first device connecting member 18. A second blocking member 84 can be provided on a portion of the rod 30 on the other side of the first device connecting member 22. The blocking members 82 and 84 can be fixed to the rod 30, or can be slidably engaged to the rod 30 and secured by suitable structure such as a set screw. Each of these blocking devices could provide progressive resistance (proportional to distance) with or without elastic properties. The blocking members 82 and 84 can be formed from a rigid material, or from an elastic material which will mimic the action of the ligaments. The elastic material can be such that a force is applied by the elastic material which is proportional to the distance traveled. Other structure is possible. Varying these parameters allows for closer reproduction of the ligament functions. The blocking devices can also prevent removal of the rod from the connectors. The blocking devices could also be connected to other parts of the construct, thus preventing any undesirable movement of the screw with respect to the vertebral body. For example, this could ensure a screw does not back out of the vertebral body. Such blocking devices could also be integral into the connector itself with the use of set screws, channels, and the like.

An installation of an artificial facet joint according to the invention is shown in FIG. 4. The invention can be utilized with any vertebra; however, there is shown the lumbar vertebrae 90, 94, and 98 adjacent to sacrum 104. The rod 30 is slidably engaged to the first connecting member 18 of the connector 14. The second device connecting member 22 is slidably engaged to the elongated shaft 70 of the pedicle screw 40. The apertures 26 and 34 can be coated with a friction reducing coating. The pedicle screw 40 is secured to the pedicle 110 of the vertebra 94. The screw 40 can be secured in the plane of the existing or former facet so as to better mimic the natural facet. If the natural facet is in existence, the artificial facet will provide reinforcement. Another connector 100 having a first device connecting member 18 and a second device connecting member 22, is connected to the pedicle 110 of the adjacent vertebra 90 by another screw 40. The provision of the connectors 14 and 100 on adjacent vertebrae with the rod 30 extending between them creates an artificial facet joint in which limited movement is permitted by the freedom of movement of the pieces of the joint, but which will not permit excessive movement. The action of the artificial facet also mimics the action of the ligaments which surround the spine to limit flexion of the spine.

The rod 30 is secured against excessive movement relative to the connectors 14 and 100 by clamping the rod 30 at some location. Any suitable structure for clamping the rod against movement is possible. There is shown in FIG. 4 a variable angle connector 120 which can be utilized. Such a connector is described in Simonson, U.S. Pat. No. 5,885,285, the disclosure of which is hereby incorporated fully by reference, however, any other suitable clamping or connection device can be utilized. The variable angle connector 120 can be secured to the spine by suitable structure such as another pedicle screw 40. The variable angle connector 120 has a set screw 122 which engages the rod 30 and prevents the rod 30 from moving relative to the variable angle connector 120.

There is shown in FIG. 4 two artificial facet joints. The connectors 14 and 100 with the rod 30 forms one joint. It is also possible to provide an artificial facet joint in which a connector 14 is provided on one adjacent vertebrae, and structure for securing the rod against axial movement relative to the spine is provided on the other adjacent vertebrae. This artificial facet joint would be formed by the connector 100 and structure for securing such as variable angle connector 120, but could be without any other connector such as connector 14. The rod 30 is thereby fixed on one side of the joint, and can slide through the connector 100 on the other side of the joint.

Figure 5:
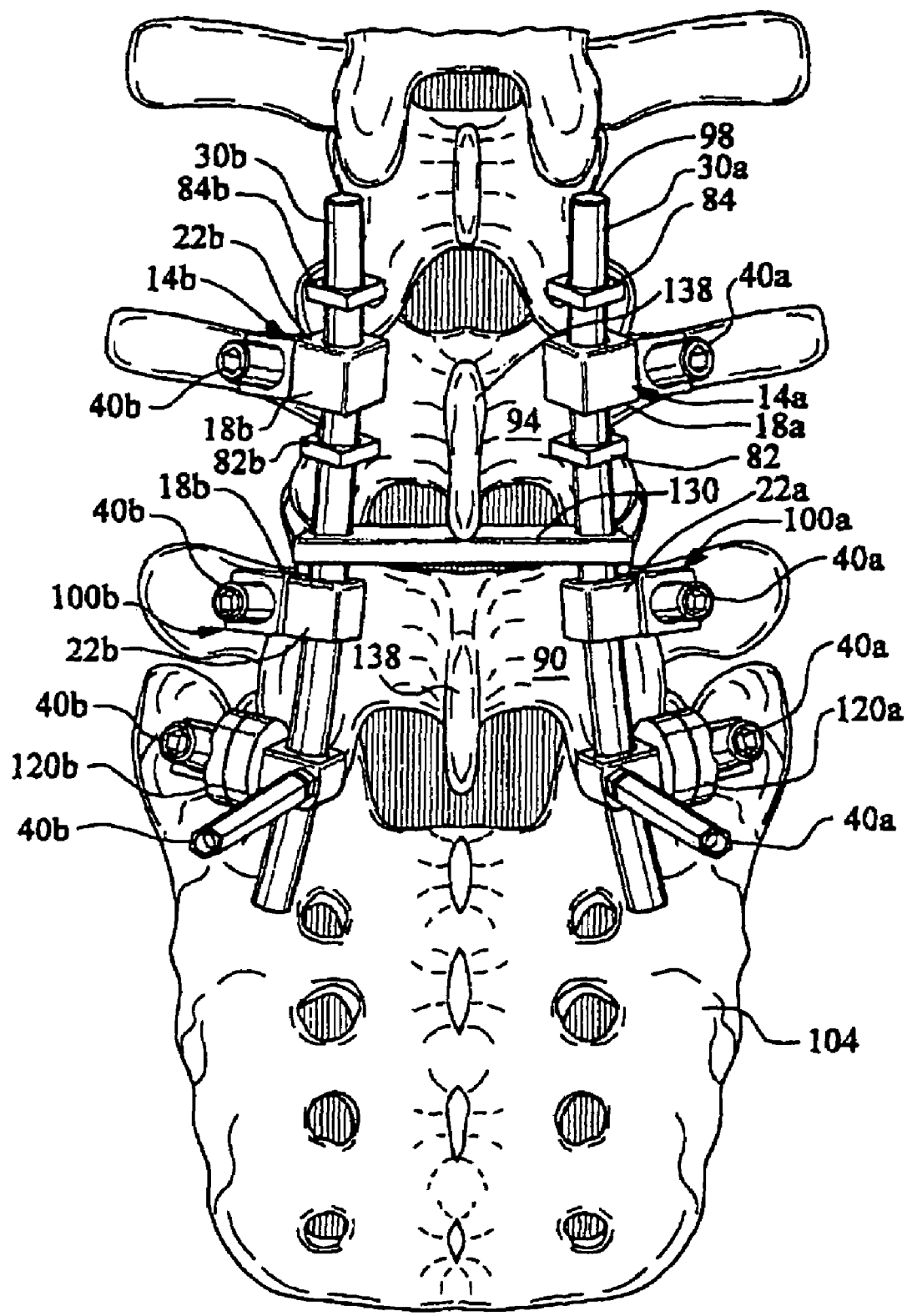
FIG. 5 is a posterior view.

An artificial facet joint is created on each lateral side of the spine, as shown in FIG. 5. There is shown another assembly with spinal rod 30b slidably engaged to connectors 14b and 100b, which are comprised of first device connecting member 18b and second device connecting member 22b, and are also slidably engaged to screws 40b. Variable angle connector 120b or other suitable structure is utilized to secure the rod 30B in position.

A transverse member 130 is engaged to rods 30a and 30b. The transverse member 130 can have apertures which slidably engage the rods 30a and 30b. Other connection means are possible. The transverse connecter may connected to the screws 40a and 40b themselves to avoid rotation of the bone screws. The transverse member 130 can be in the form of a plate as shown or in any other suitable shape. The transverse member 130 provides torsional stability between the lateral sides of the artificial facet joint. The transverse member can be located between the spinous process 138 of the adjacent vertebrae 90 and 94.

The invention is made of suitable material such as surgical grade stainless steel. Any bio-compatible material with suitable strength can be utilized. The tolerances of the artificial facet joint can be created by variously sizing the rod 30, the screws 40, and the relative size of the apertures. Similarly, the transverse member 130 can be provided with apertures which permit a certain amount of movement. The amount of movement that will be appropriate will depend on the patient, the condition that is being treated, and the location in the spine where the artificial facet joint is located. Some portions of the spine are optimally more flexible than others. The connecting members could be differently dimensioned to provide different strength/flexibility characteristics. The connectors can also be variously sized to accommodate different implantation situations. Connectors can have different sizes to provide different rod to screw distances in the artificial joint. Also, connectors with adjustable distances between the first device connecting member and the second device connecting member can be provided, such as with a threaded connection which can be used to move the two members closer or farther apart.

Figure 6:
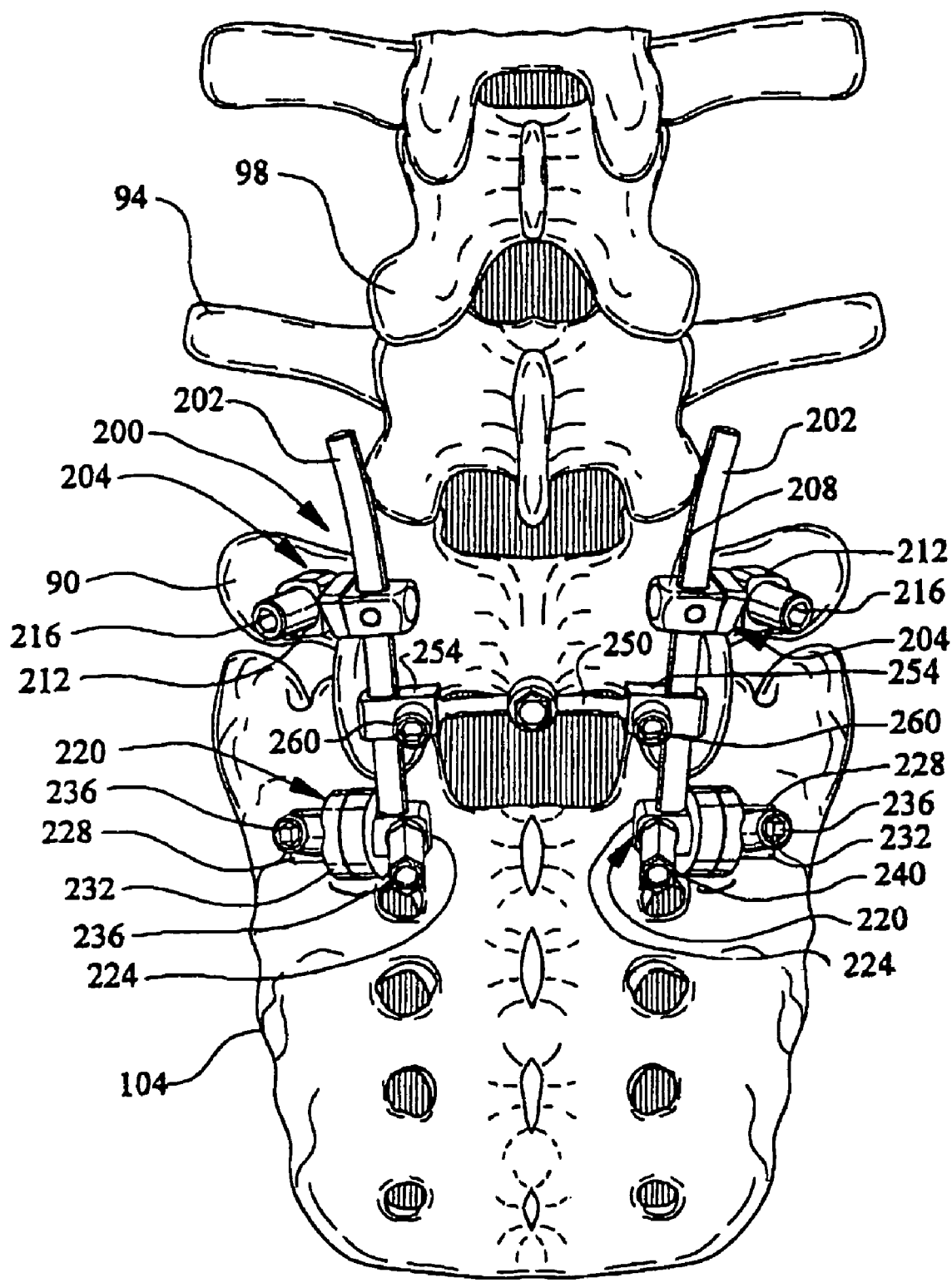
FIG. 6 is a plan view of an alternative embodiment.
Figure 7:
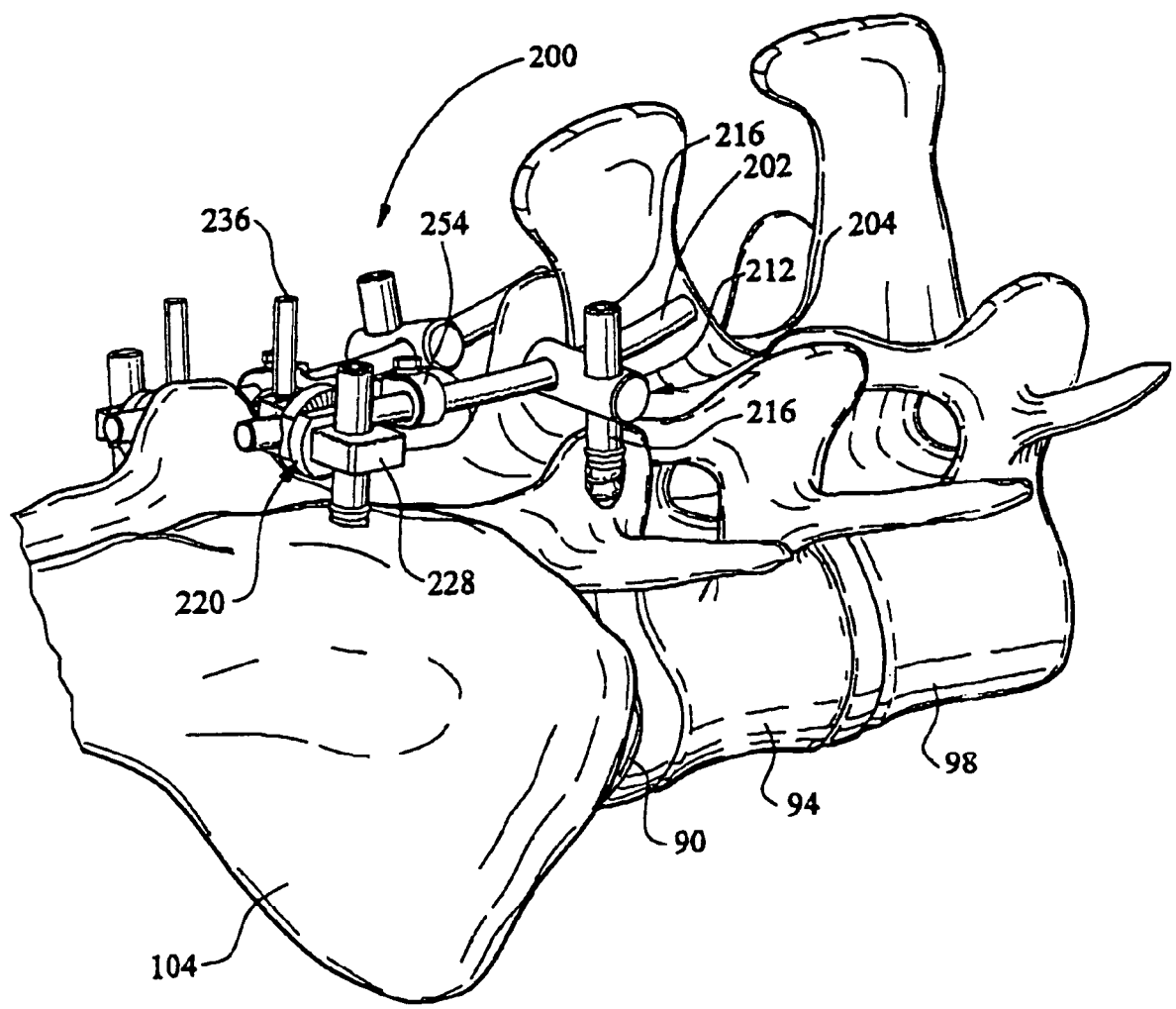
FIG. 7 is a side elevation.

There is shown in FIGS. 6-7 an artificial facet joint 200 having spinal implant rods 202. Sliding connectors 204 engage the rods 202 and permit sliding movement therebetween. Each connector 204 can be constructed to enable pivoting movement of the rod 202 relative to the connector 204. The connectors 204 can have a first connecting member 208 for engaging the rods 202 and a second connecting member 212 for engaging screws 216. The first connecting member 208 is pivotable relative to the second connecting member 212.

Fixation connectors 220 engage the rods 202 to prevent sliding movement therebetween. The fixation connectors can include a first connecting member 224 for engaging the rod 202 and a second connecting member 228 for engaging associated screws 236. The fixation connectors can include interengagement structure 232 for locking the position of the first connecting member 224 relative to the second connecting member 228, and thereby the rod 202 with respect to the screw 236. The rod 202 can be secured substantially parallel to the long axis of the spinal column.

A transverse cross-linking member 250 can be provided to connect the rods 202 and provide the joint with greater stability. End portions 254 can engage rods 202 to permit sliding movement of the transverse member 250 relative to the rods 202. Suitable structure such as set screws 260 can alternatively be used to secure the transverse member 250 in a desired position on the rods 202. The transverse member 250 can be positioned to engage the connectors 204 to limit the range of sliding movement of the rods 202 relative to the connectors 204. The transverse cross-linking member 250 can be made of a material such as an elastic material so as to provide progressive resistance to changes in the distance between the rods 202.

Figure 8:
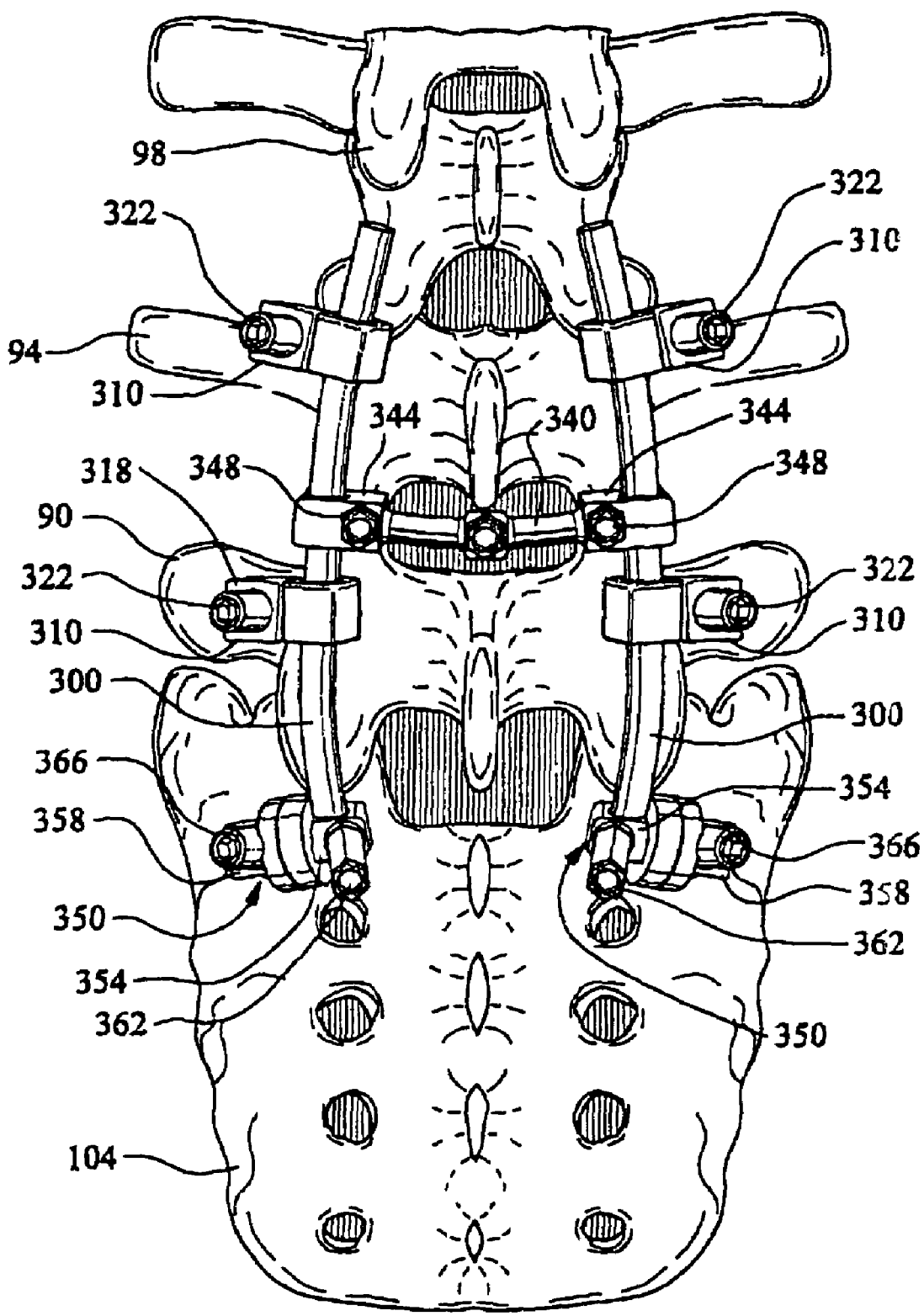
FIG. 8 is a plan view of yet another embodiment.
Figure 9:
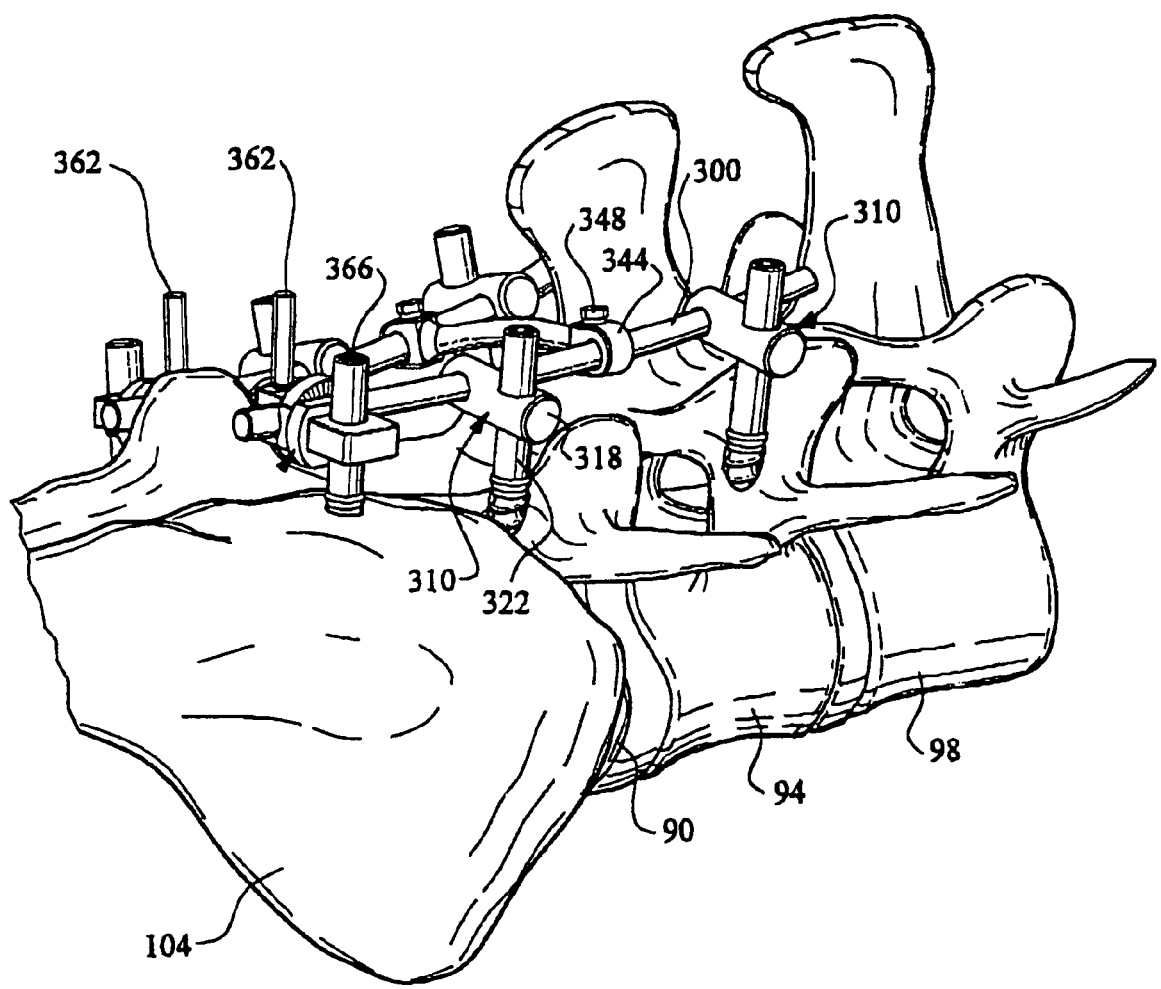
FIG. 9 is a side elevation.

Another embodiment of an artificial facet joint is shown in FIGS. 8-9. The artificial facet joint includes rods 300 engaged by sliding connectors 310. The connectors 310 can have a first device connecting member 314 for engaging the rods 300 and second device connecting members 318 for engaging screws 322. The connectors 310 are secured to the vertebrae 90, 94 by the screws 322. The first device connecting members 314 engage the rods 300 so as to permit sliding movement of the rods 300 relative to the first device connecting members 314. The first device connecting members 314 pivot relative to the second device connecting members 318 to permit pivoting of the rods 300 relative to the screws 322.

Fixation connectors 350 secure the rods 300. A rod connecting member 354 can have suitable structure for engaging the rod 300 such as set screw 362. A screw connecting member 358 engages the screw 366. The screw connecting member 358 is pivotable relative to the rod connecting member 354. The rods 300 are thereby pivotable in the sagittal plane.

A transverse cross-linking member 340 can be provided and secured between the rods 300 to provide stability to the joint. Ends 344 can be joined to the rods 300 so as to permit sliding movement, or suitable structure such as set screws 348 can be provided to prevent sliding movement. The transverse member 340 can be positioned on the rods 300 so as to contact connecting members 310 to prevent excessive movement of the rods 300 relative to the connectors 310. The rods 300 can span three or more vertebrae as the implantation may require.

Figure 10:
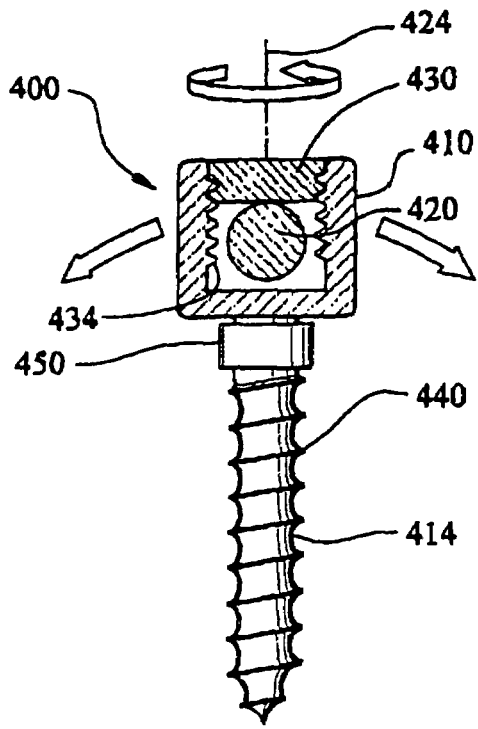
FIG. 10 is front elevation of still another embodiment.
Figure 11:
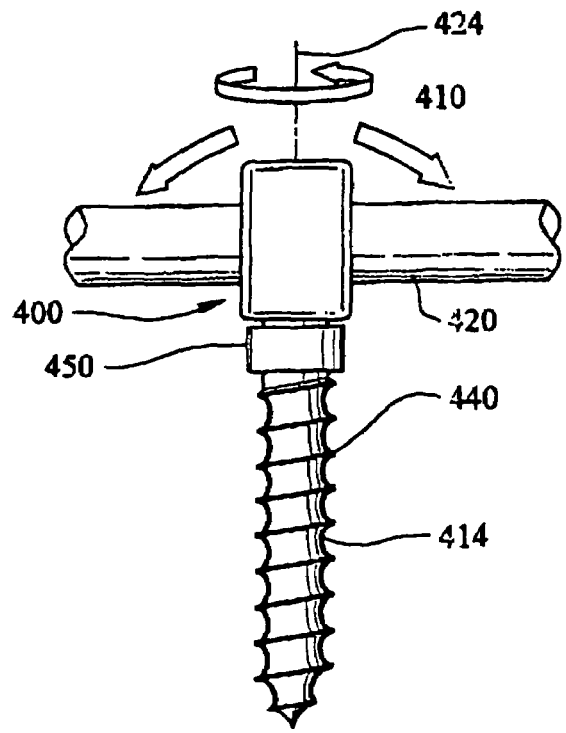
FIG. 11 a side elevation.
Figure 12:
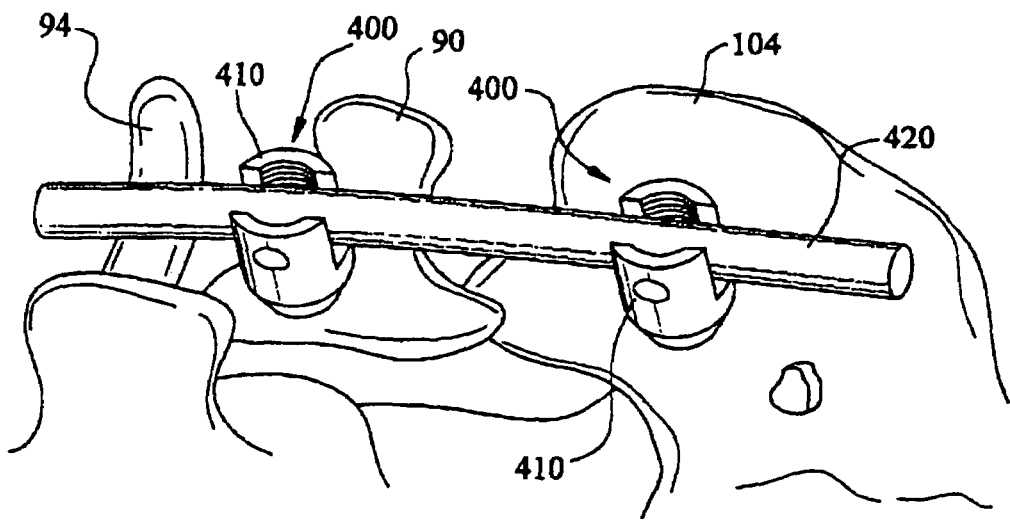
FIG. 12 is a perspective view as implanted in a spine.

There is shown in FIGS. 10-12 an alternative connector for an artificial facet joint according to an alternative embodiment of the invention. The connector 400 has a head portion 410 and a screw portion 414. The head portion 410 is capable of sliding engagement of a spinal rod 420. The head portion 410 is pivotally connected to the screw portion 414. The head portion 410 can be polyaxially pivotable with respect to the screw portion, such that the head portion can pivot with respect to the long axis 424 of the screw portion 414 as shown by the arrows in FIGS. 10-11. The pivoting connection can be provided by any suitable structure, such as a ball-and-socket joint. Also, the head portion 410 can be joined to the screw portion 414 to permit rotation of the head portion 410 about the long axis 424 as shown. Further, the head portion 410 can be detachably connected to the screw portion 414 by the provision of removable engagement structure such as a nut which engages a post on the screw portion 414. The rod can be of any suitable shape. In one embodiment, the rod can be a plate with a groove through which extends the polyaxially pivotable screws.

The head portion 410 can have any suitable structure for engaging the rod 420. In the embodiment shown in FIGS. 10-12, the head portion 410 has a cup or saddle shape for receiving the rod 420. A cap 430 can be engaged to the head portion by suitable structure such as threads 434 to secure the rod 420 within the head portion 410. Threads 440 on the screw portion 414 can be provided to engage the screw portion 414 to the vertebrae.

The degree of angulation of the head portion 410 with respect to the long axis 424 of the screw portion 414 can be limited by suitable structure such as a stop 450. As the head portion 410 pivots with respect to the screw portion 414, the head portion will contact the stop 450 to prevent or retard further pivoting. The stop can be integral with the screw portion 414 or attached to the screw portion 414 by suitable means such as welding, adhesives, or set screws. The resistance provided by the stop 450 can be progressive such that increased angulation of the head portion 410 with respect to the screw portion 414 will result in increased resistance. The stop 450 can be made of an elastic material which will provide increased resistance as contact with the head portion 410 increases the compression of the elastic material. It is alternatively possible to limit pivoting movement of the head portion 410 with respect to the screw portion 414 by other structure, such as projections on the head portion 410 which contacts the stop 450, or cooperating structure on the screw portion 414 or the rod 420. Further, elastic material can be provided on the rod, such as in the form of an tube that is fitted over the rod 420, to contact the connector and limit the motion of the artificial facet joint.

The implantation of the connectors 400 is shown in FIG. 12. The screw portion 414 is engaged to the vertebrae 90 and/or sacrum 104. The rod 420 is positioned in the channels of the head portions 410. The caps 430 can then be secured to the head portions 410 to secure the rod 420 in place. Suitable clamping structure can be provided to secure the rod 420 against sliding movement. The caps 430 can be tightened to clamp the rod 420, or can form a channel for permitting sliding movement. A connector 410 at the lowermost vertebrae or the sacrum can be used to clamp the rod 420, while connectors 410 that are secured to upper vertebrae can permit sliding movement to permit the spinal column to move within the limits of the artificial facet joint. The connectors 410 and rod 420 can all be implanted through percutaneous incisions.

The spinal implant rods used in the artificial facet joints of the invention can be of any suitable construction, shape, material and length. The rods can be bent in a shape which will essentially guide the connectors in sliding movement along the rod. The spine will thereby be directed by the rod to flex according to a path and limits that are determined to be best suited for the particular patient. The connectors can have a fixed angle relative to the rod connecting portions and screw connecting portions, or can have structure which will limit the angulation, to provide that the connectors follow the spinal rod according to the desired path. The screws can be angled or shaped so as to provide a guide path for bending of the spine. A barrier device can be provided in a suitable form such as a plastic cover to reduce the contact between the artificial facet joint and surrounding tissue.

This invention can be embodied in other forms without departing from the spirit or essential attributes thereof and, accordingly, reference should be had to the following claims rather than the foregoing specification as indicating the scope of the invention.

I claim:

1. A method for dynamically supporting the spine in the area of the facet joint, comprising the steps of:

providing a spinal implant rod;

providing at least a fixation connector assembly and a sliding connector assembly, each said connector assembly comprising a post and a connecting member having a rod connecting portion and a post connecting portion, said sliding connector assembly having a rod connecting portion with structure for slidable engagement of said rod, said fixation connector assembly having a rod connecting portion with structure for engaging said rod so as to prevent sliding movement of said rod relative to said connector assembly;

positioning and securing said post of said sliding connector assembly or said fixation connector assembly in the area of the superior articular facet of a lower vertebrae, and positioning and securing said post of the other of said sliding connector assembly or said fixation connector assembly in the area of an inferior articular facet of an adjacent upper vertebrae; and, securing said rod to said sliding connector assembly so as to be slidable relative thereto postoperatively, and securing said rod to said fixation connector assembly so as to prevent slidable movement relative thereto postoperatively.

2. The method of claim 1, wherein a portion of said connecting member pivots to permit pivoting of said rod about an axis transverse to a long axis of said post.

3. The method of claim 2, wherein each rod connecting portion is pivotally engaged to said post connecting portion and said rod connecting portion and said rod pivot about an axis transverse to a long axis of said post.

4. The method of claim 1, wherein said post connecting portion slides relative to said post along a long axis thereof.

5. The method of claim 1, wherein the post comprises a screw portion, said securing step comprising screwing said screw portion into said vertebrae.

6. The method of claim 1, wherein said connecting member pivots polyaxially relative to the rod.

7. The method of claim 1, further comprising the step of increasing resistance to angulation as the degree of angulation increases.

8. The method of claim 1, further comprising the step of securing a second sliding connector assembly, a second fixation connector assembly, and a second rod to an opposite lateral side of said vertebrae by positioning and securing said post of said second sliding connector assembly or said second fixation connector assembly in the area of the superior articular facet of a lower vertebrae, and positioning and securing said post of the other of said second sliding connector assembly or said second fixation connector assembly in the area of an inferior articular facet of an adjacent upper vertebrae; and, securing said second rod to said sliding connector assembly so as to be slidable relative thereto postoperatively, and securing said second rod to said second fixation connector assembly so as to prevent slidable movement relative thereto postoperatively.

9. The method of claim 8, further comprising the step of attaching a crosslinking member to and between said spinal rods.

10. The method of claim 1, wherein said spinal rod is positioned so as to be substantially parallel to the spinal column.

11. The method of claim 1, wherein said spinal rod articulates in the sagittal plane.

12. The method of claim 1, wherein said rod is shaped to define a desired bending of the spine, such that bending of the spine causes sliding movement of the connector relative to said rod, and said rod guides said connector according to a path defined by said rod.

13. The method of claim 1, wherein said connecting member is movable over the screw, and the screw is shaped to provide a path and guides the motion of the spine during bending of the spine.

* * * * *